(12) United States Patent
Morgan, Jr.

(10) Patent No.: US 8,752,550 B2
(45) Date of Patent: Jun. 17, 2014

(54) INTERNAL NOSE FILTER MOUNTING DEVICE, METHOD, AND KIT

(75) Inventor: Toby S. Morgan, Jr., Rome, GA (US)

(73) Assignee: Toby S. Morgan, Jr., Rome, GA (US)

( * ) Notice: Subject to any disclaimer, the term of this patent is extended or adjusted under 35 U.S.C. 154(b) by 62 days.

(21) Appl. No.: 13/542,894

(22) Filed: Jul. 6, 2012

(65) Prior Publication Data

US 2014/0007880 A1   Jan. 9, 2014

(51) Int. Cl.
*A61G 10/00* (2006.01)
*A61M 16/00* (2006.01)

(52) U.S. Cl.
USPC ................................. 128/206.11; 128/205.27

(58) Field of Classification Search
USPC ............ 128/200.24, 200.26, 201.13, 201.25, 128/205.27, 205.29, 206.11, 206.16, 128/206.17, 206.18, 206.19; 606/183–186, 606/188
See application file for complete search history.

(56) References Cited

U.S. PATENT DOCUMENTS

| 4,105,035 | A | 8/1978 | Rella |
| 5,850,834 | A | 12/1998 | Yoshida et al. |
| 5,947,119 | A | 9/1999 | Reznick |
| 6,213,121 | B1 | 4/2001 | Cardarelli |
| 7,263,996 | B2 | 9/2007 | Yung Ho |
| 7,318,438 | B2 | 1/2008 | Brown |
| 2004/0147954 | A1 | 7/2004 | Wood |

OTHER PUBLICATIONS

International Search Report and Written Opinion for International Application No. PCT/US2013/048251, mailed Oct. 21, 2013.

*Primary Examiner* — Melanie Hand
*Assistant Examiner* — Aundria Hairell
(74) *Attorney, Agent, or Firm* — Sutherland Asbill & Brennan LLP

(57) ABSTRACT

Internal nose filter mounting devices, methods and kits are provided. The nose filter mounting device includes two substantially parallel elongated members having first and second ends, a first connecting member joining the two elongated members at or near the first ends, a second connecting member joining the two elongated members at or near the second ends, and first and second magnets connected to the first and second connecting members, wherein the first and second magnets are configured to mate with filter elements in the nostrils of a user. The device may be implanted in the nasal septum of a patient.

29 Claims, 4 Drawing Sheets

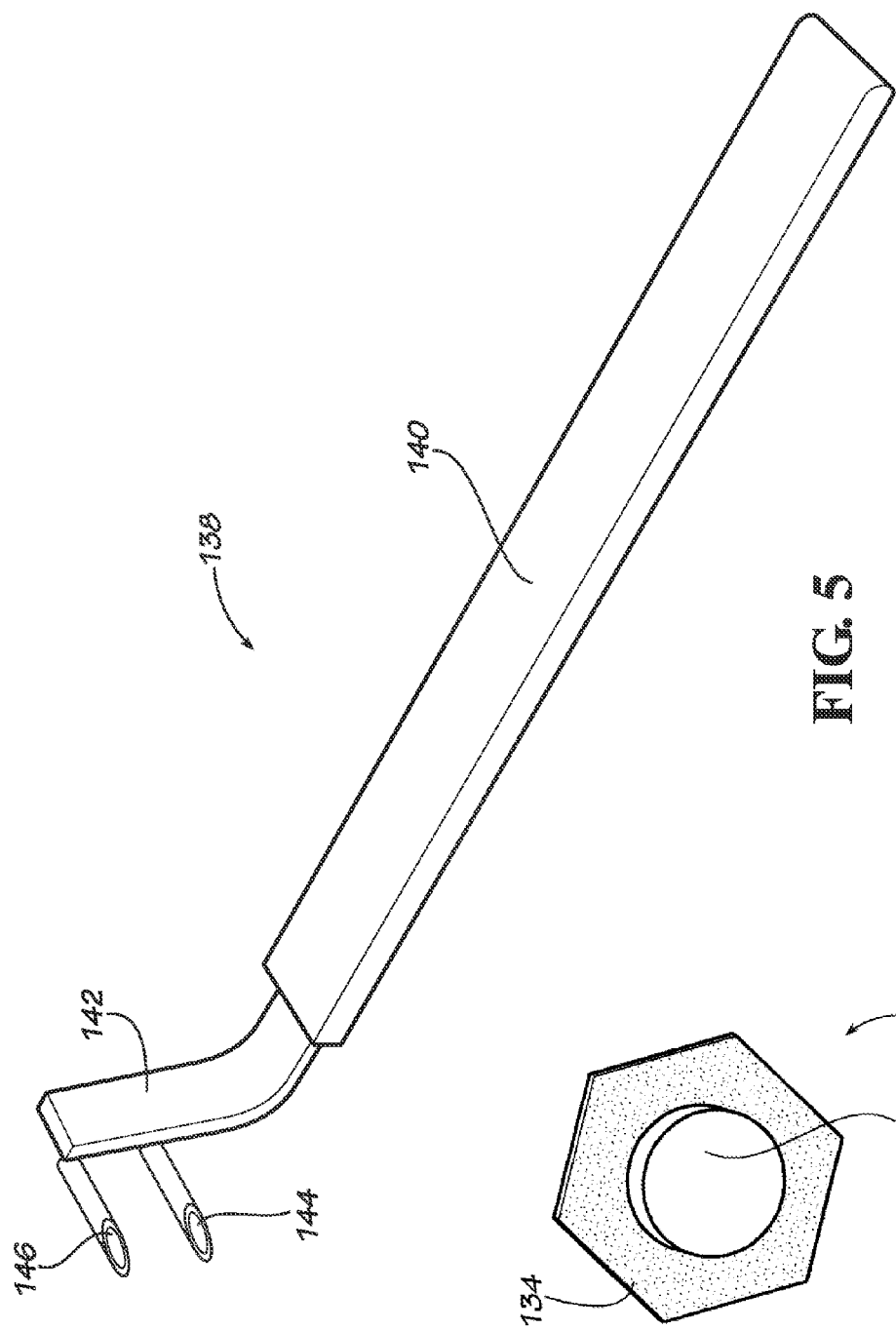

INTERNAL NOSE FILTER MOUNTING DEVICE, METHOD, AND KIT

TECHNICAL FIELD

The present invention relates generally to the field of filtration devices for nasal passages, and more particularly to internal magnetic nose filter mounting devices, kits, and methods for use thereof.

BACKGROUND

Global air contamination is worsening each year and an increased number of persons are suffering medical problems due to the inhalation of contaminants. For example, airborne contaminants may include the output from factories, combustion exhaust from vehicles, sand in desert climates, and chemicals and other toxins in workplaces. Additionally, many people suffer from allergies to pollens, dust, grasses, molds, and other airborne allergens.

The majority of inhaled air, including airborne allergens and contaminants, enters the body through the nose. Exposure to such contaminants may result in severe rhinitis, postnasal drip, nasal polyps, nasal obstruction, sinusitis, asthma, bronchitis, COPD, and various other conditions that may necessitate treatments including antibiotics, antihistamines, nasal sprays, and oral and/or injected steroids. Allergy sufferers may require extensive allergy testing to determine the nature of their allergies. In some cases, medicinal treatments are not sufficient and surgery of the nose and/or sinuses is necessary to obtain relief for a patient.

Various nose filters are known that allow air to be filtered prior to inhalation through the nose and/or mouth. For example, devices such as face masks and adhesive filters that adhere to the outer surface of the nostrils allow air to be filtered prior to inhalation by a wearer. However, such filters experience problems such as user discomfort and irritation of the sensitive nasal tissues. Additionally, these filters are visible to others and are not aesthetically attractive. Furthermore, these filters may not be suitable for use in all situations.

Filtration devices that are worn within the nostrils of a user are also known. For example, U.S. Pat. No. 6,213,121 to Cardarelli discloses a surgically implantable nasal filtration device. The device relies on a complex design including three sleeves, two smaller and one large, that are punched through the septum. A pair of stabilizer plates distributes stresses and a large septum stud supports snap-on filter elements. However, the size and complex design of the device make it difficult to implant and remove, and possibly painful for wearers. For example, the device requires a large hole in the anterior/cartilaginous septum, which can result in severe discomfort and nasal bleeding, and cause whistling while breathing if the hole persists after removal of the device.

Accordingly, it would be desirable to provide devices and methods to improve the comfort and aesthetics of nasal filtration.

SUMMARY

Devices, methods, and kits for nasal filtration are provided. In one aspect, a nose filter mounting device is provided. The device includes two substantially parallel elongated members having a first end and a second end and a cross-sectional width less than about 3 mm, a first connecting member joining the two elongated members at or near the first ends, and a second connecting member joining the two elongated members at or near the second ends. A first magnet is connected to the first connecting member and a second magnet is connected to the second connecting member. The first and second magnets are configured to mate with filter elements in the nostrils of a user. The device may further include a mating member operable to secure the second connecting member at or near the second ends of the two elongated members.

In another aspect, a method for implanting a nose filter mounting device is provided. The method includes providing a pronged article and a second connecting member, piercing a nasal septum of a patient with a septum piercing device to provide two septum apertures, inserting the pronged article through the two septum apertures, and positioning the second connecting member on the pronged article. The pronged article has two substantially parallel elongated members having a first and a second end and a cross-sectional width less than about 3 mm, a first connecting member joining the two elongated members at or near the first ends, and a first magnet connected to the first connecting member. The second connecting member has a second magnet connected thereto. The second connecting member is positioned on the two elongated members of the pronged article such that the two elongated members are joined at or near the second ends.

The second connecting member may have two apertures therein, the apertures being configured to fit on the two elongated members. In one embodiment, the step of positioning the second connecting member includes positioning the two apertures of the second connecting member on the two elongated members. The method may also include securing the second connecting member on the two elongated members with a mating member positioned at or near the second ends of the two elongated members.

In a third aspect, a kit is provided. The kit includes a septum piercing device, a pronged article, and a second connecting member. The septum piercing device includes an elongated portion, an end portion sized and shaped to fit inside the patient's nostril and located at one end of the elongated portion, and two parallel hollow needles affixed on the end portion and having an outside diameter of about 3 mm or less. The pronged article includes two substantially parallel elongated members having a first and a second end and a cross-sectional width less than about 3 mm, a first connecting member joining the two elongated members at or near the first ends, and a first magnet connected to the first connecting member. The second connecting member is configured to join the two elongated members at or near the second ends and having a second magnet connected thereto. The kit may also include a mating member operable to secure the second connecting member at or near the second ends of the two elongated members.

BRIEF DESCRIPTION OF THE DRAWINGS

FIG. 5 is a perspective view of a nasal septum piercing device in accordance with one or more embodiments of the present invention.

FIG. 6 is a perspective view of a filter element in accordance with one or more embodiments of the present invention.

DETAILED DESCRIPTION

The present application will now be described more fully hereinafter with reference to the accompanying drawings, in which several embodiments of the application are shown. Like numbers refer to like elements throughout the drawings.

Mounting Device

Figure 2A:
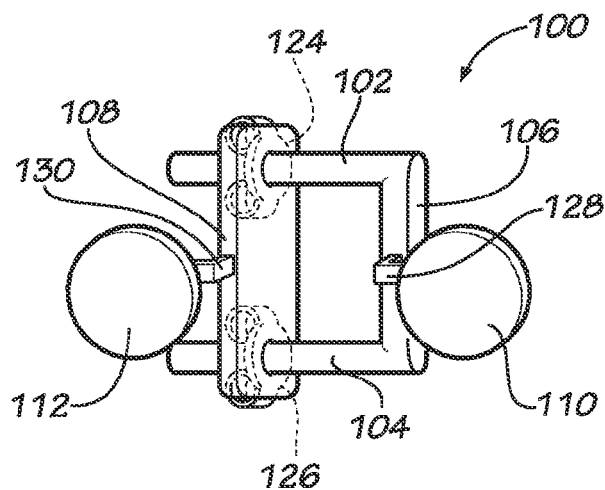
FIG. 2A is a perspective view of an assembled nose filter mounting device in accordance with one or more embodiments of the present invention.
Figure 2B:
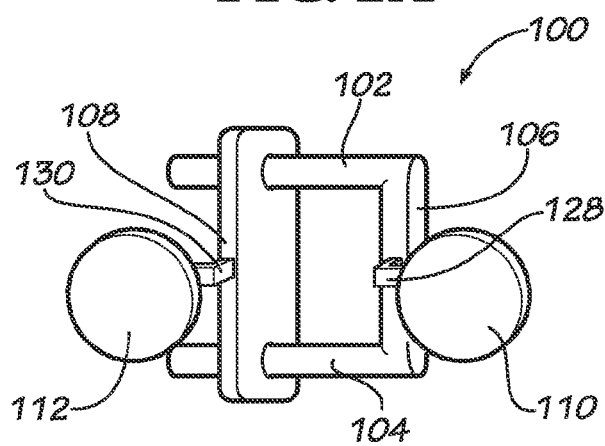
FIG. 2B is a perspective view of an assembled nose filter mounting device in accordance with one or more embodiments of the present invention.
Figure 3:
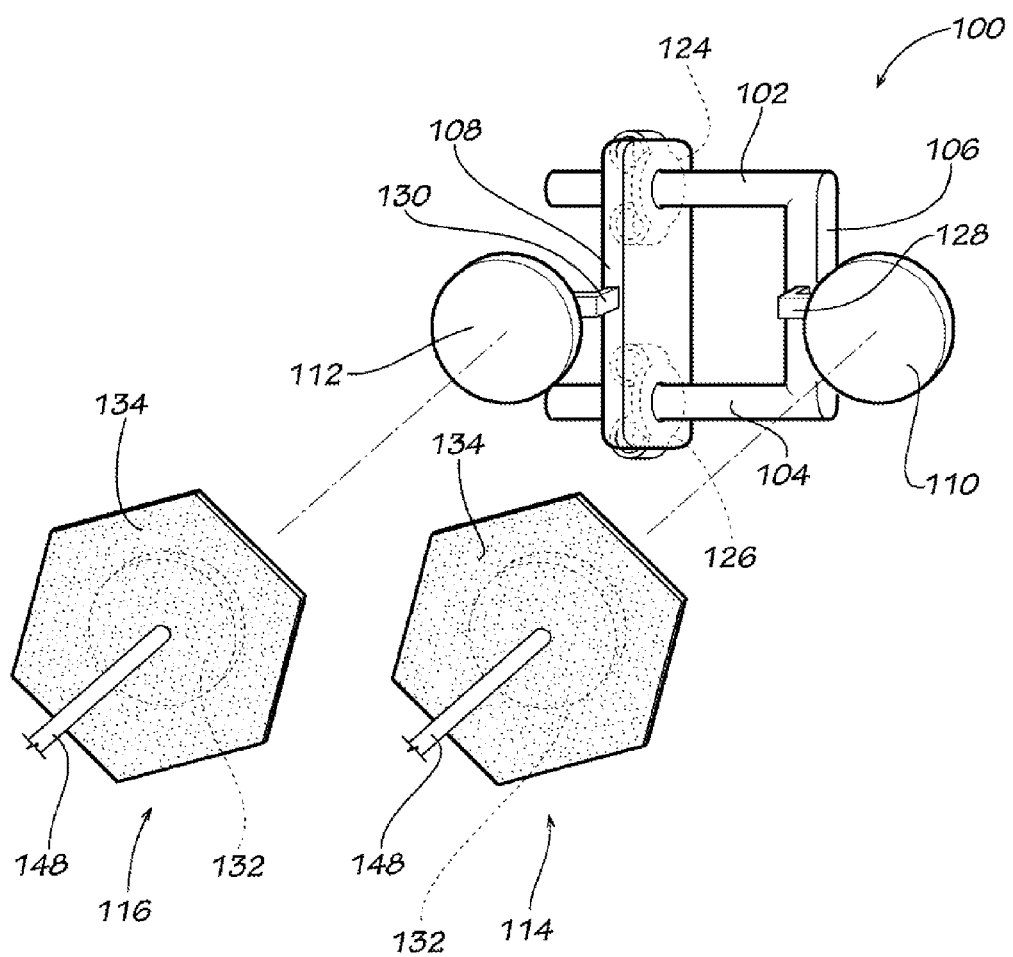
FIG. 3 is a perspective view of an assembled nose filter mounting device and filter elements in accordance with one or more embodiments of the present invention.

In one aspect, as shown in FIGS. 1-4, an internal nose filter mounting device 100 is provided. In one embodiment, the mounting device 100 includes two substantially parallel elongated members 102, 104 having a first end and a second end, a first connecting member 106 joining the two elongated members 102, 104 at the first ends, and a second connecting member 108 joining the two elongated members 102, 104 at the second ends. A first magnet 110 may be connected to the first connecting member 106 and a second magnet 112 may be connected to the second connecting member 108. In one embodiment, the first and second magnets 110, 112 are configured to mate with filter elements 114, 116 in the nostrils of a user, as shown in FIG. 3.

Figure 4A:
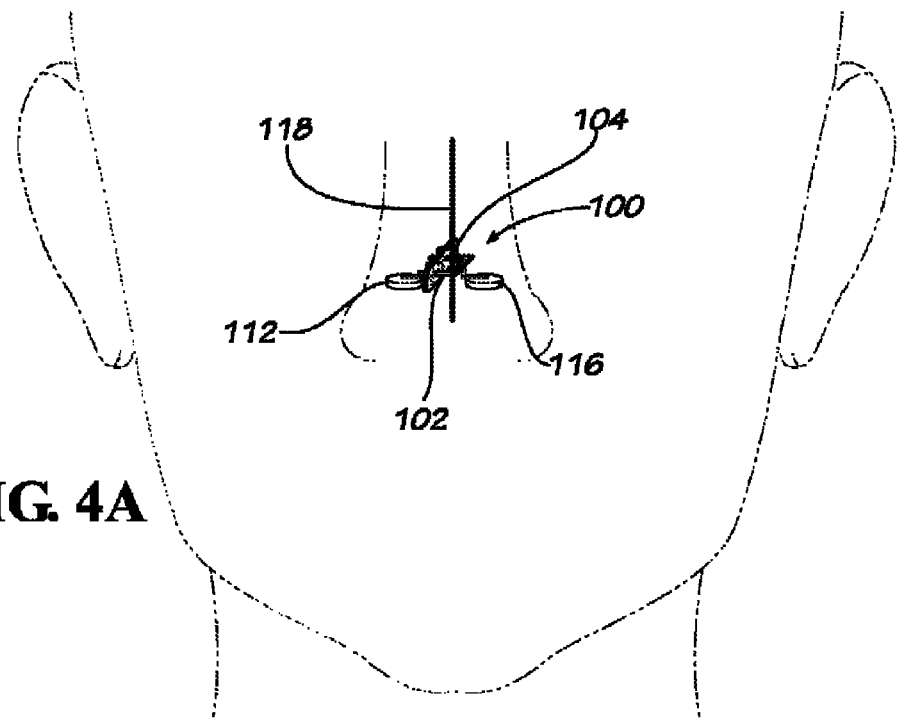
FIG. 4A is a perspective view of an implanted nose filter mounting device in accordance with one or more embodiments of the present invention.

As shown in FIG. 4A, the mounting device 100 is configured such that it may be implanted in the nasal cavity of a patient. For example, the elongated members 102, 104 may be implanted through the nasal septum 118 of a patient. The two elongated members may be substantially parallel. As used herein, the tem "substantially parallel" refers to the two elongated members being parallel or almost parallel.

The elongated members may be sized and shaped to fit within the nasal cavity of a patient. For example, the elongated members may have a size and shape such that they may be implanted through the nasal septum of a patient without causing significant trauma or leave a large perforation on removal which could result in bleeding or whistling while breathing. The elongated members may have a cross-sectional width between about 3 mm and about 0.5 mm. For example, the elongated members may have a cross-sectional width of less than about 3 mm, less than about 2 mm, or less than about 1 mm. In one embodiment, the elongated members have a cross-sectional width of about 1 mm.

The elongated members may have a polygonal, circular, rectangular, triangular, elliptical, or otherwise shaped cross-section. For example, the two elongated members may each have a circular cross section and be substantially cylindrical. In certain embodiments, the elongated members may have a cross-section that is square, star, octagon or hexagon shaped. Other cross-sectional shapes may also be used and would be known to one of ordinary skill in the art. In one embodiment, the elongated members may be tapered. For example, the elongated members may have a larger cross-sectional width at the first ends than at the second ends.

Figure 1:
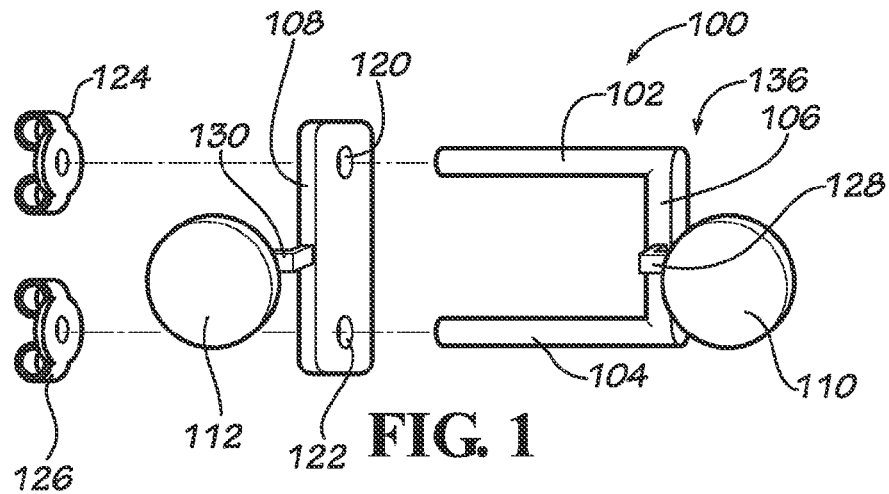
FIG. 1 is a perspective view of a disassembled nose filter mounting device in accordance with one or more embodiments of the present invention.

As shown in FIGS. 1-2, a first connecting member 106 joins the two elongated members 102, 104 at the first ends. Alternatively, the first connecting member may join the elongated members near the first ends. In one embodiment, the first connecting member is substantially perpendicular to the two elongated members. As used herein, the term "substantially perpendicular" refers to the first connecting member being perpendicular or almost perpendicular to the two elongated members. For example, when the device is implanted in the nasal cavity of a patient, the first connecting member may be substantially parallel to the nasal septum and lie flat against it.

The first connecting member may be sized and shaped to fit within the nasal cavity and connect the two elongated members. For example, the first connecting member may have a polygonal, circular, rectangular, triangular, elliptical, or otherwise shaped cross-section. The first connecting member may have a width that is larger than the cross-sectional width of the two elongated members. The first connecting member may have a width between about 2 mm and about 15 mm. For example, the first connecting member may have a width that is less than about 15 mm, less than about 10 mm, or less than about 3 mm. The first connecting member may have a length between about 5 mm and about 15 mm. For example, the first connecting member may have a width that is less than about 15 mm, less than about 10 mm, or less than about 6 mm. The first connecting member may have a thickness between about 1 mm and about 5 mm. For example, the first connecting member may have a width that is less than about 5 mm, less than about 3 mm, or less than about 1 mm. In one embodiment, the first connecting member may have a rectangular cross-section and a width of about 2 mm, a length of about 10 mm, and a thickness of about 1 mm.

In certain embodiments, more than two parallel elongated members may be included in the device. For example, the device may include two sets of parallel elongated members, each connected by a first connecting member, the two first connecting members being connected by an additional connecting member.

Figure 4B:
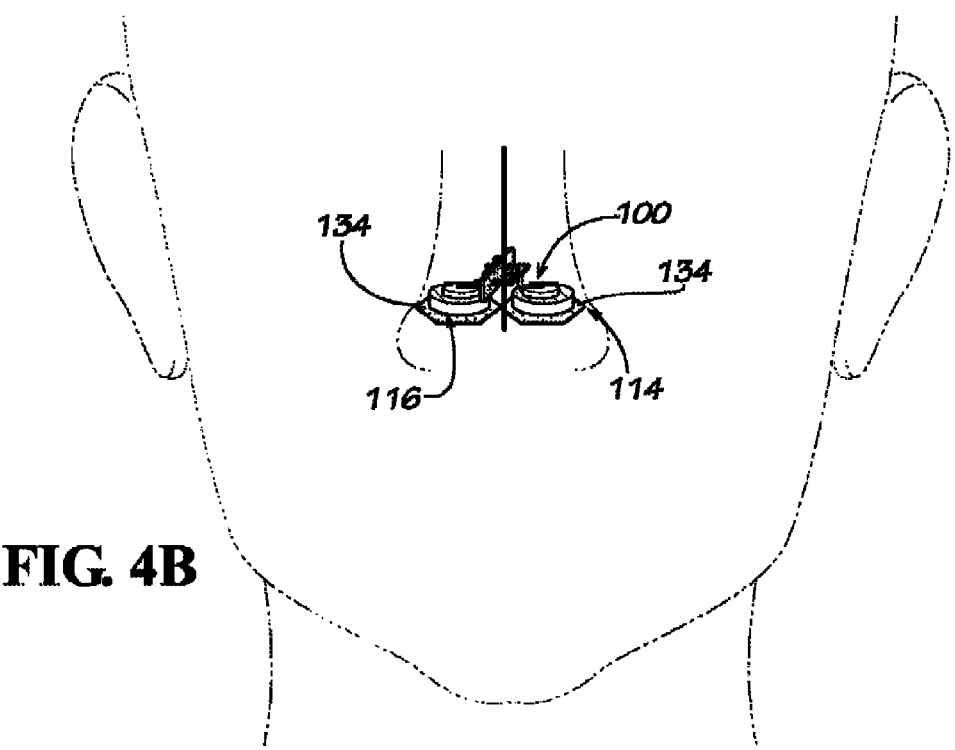
FIG. 4B is a perspective view of an implanted nose filter mounting device with mounted filter elements, in accordance with one or more embodiments of the present invention.

As shown in FIGS. 2-4, a second connecting member 108 joins the two elongated members 102, 104 at the second ends. Alternatively, the second connecting member may join the elongated members near the second ends. In one embodiment, the second connecting member is substantially perpendicular to the two elongated members. For example, when the device is implanted in the nasal cavity of a patient, the second connecting member may be substantially parallel to the nasal septum and flat against it or adjacent to it, as shown in FIGS. 4A-B.

The second connecting member may be sized and shaped to fit within the nasal cavity and connect the two elongated members. For example, the second connecting member may have a polygonal, circular, rectangular, triangular, elliptical, or otherwise shaped cross-section. The second connecting member may have a cross-sectional width that is larger than the cross-sectional width of the two elongated members. The second connecting member may have a width between about 2 mm and about 15 mm. For example, the second connecting member may have a width that is less than about 15 mm, less than about 10 mm, or less than about 3 mm. The second connecting member may have a length between about 5 mm and about 15 mm. For example, the second connecting member may have a width that is less than about 15 mm, less than about 10 mm, or less than about 6 mm. The second connecting member may have a thickness between about 1 mm and about 5 mm. For example, the second connecting member may have a width that is less than about 5 mm, less than about 3 mm, or less than about 1 mm. In one embodiment, the second connecting member may have a rectangular cross-section and a width of about 2 mm, a length of about 10 mm, and a thickness of about 1 mm.

In certain embodiments, the second connecting member has two apertures 120, 122 therein, the apertures 120, 122 being configured to fit on the two elongated members 102, 104, as shown in FIG. 1. For example, the apertures may have a similar shape to the cross-section of the elongated members. The apertures may be sized slightly larger than the cross-section of the elongated members to accommodate the elongated members therein. The apertures may have a diameter of between about 0.5 mm and about 3 mm. For example, the apertures may have a diameter of less than about 3 mm, less than about 2 mm, or less than about 1 mm. In one embodiment, the apertures have a diameter of about 1 mm.

The device may also include a mating member that is operable to mate with the elongated members and secure the second connecting member at or near the second ends of the two elongated members. In one embodiment, the mating member includes two apertures that are capable of securing on the elongated members. In another embodiment, the mating member includes two cavities in which the second ends of the elongated members can be received. For example, the mating member may include one or more clamping, locking, coupling, frictional engagement, or other mechanisms that allow the mating member to secure onto the elongated members. The elongated members may have notches near the end to assist in securing them to the mating elements similar to those employed on the connecting rods of pierced earrings.

In one embodiment, as shown in FIG. 2B, the mating member is integral with the second connecting member 108. For example, the second connecting member may include two apertures, each having a clamping mechanism therein that allows the second connecting member to secure onto the elongated members. In another example, the second connecting member may include two apertures that are sized to frictionally engage with the elongated members, allowing the second connecting member to secure thereon.

In another embodiment, as shown in FIG. 2A, the mating member includes two distinct mating elements 124, 126, similar to pierced earring backings or clamps, each mating element operable to secure on the second end of one of the two elongated members 102, 104. For example, the two distinct mating elements may each include a clamping, locking, coupling, frictional engagement, or other mechanism that allows the mating element to secure onto the second end one of the elongated members. The distinct mating elements may be tubular in form and display size and material properties that allow the distinct mating element to frictionally engage the second end of one of the two elongated members.

As shown in FIGS. 1-4, first and second magnets 110, 112 may be connected to the first and second connecting members 106, 108, respectively. For example, the first and second magnets may be connected to the first and second connecting members on the outward facing surfaces, relative to the device. That is, when the device is implanted in the nasal cavity of a patient, the first and second magnets may be connected to the first and second connecting members such that the magnets are distal from the septum and facing the nostril openings. This design advantageously reduces and distributes the forces on the elongated members, and therefore the septum of a wearer.

In certain embodiments, the first and second magnets 110, 112 are connected to the first and second connecting members 106, 108 via filaments 128, 130, as shown in FIGS. 1-4. The filaments 128, 130 may be flexible or rigid in nature and may be formed of any biocompatible materials known to persons of ordinary skill in the art. For example, the filaments 128, 130 may be formed of a metal, such as titanium or gold, or a polymeric material, such as a silicone-based material. The filaments may be connected to the first and second connecting members on the outward facing surfaces, relative to the device. That is, when the device is implanted in the nasal cavity of a patient, the filaments may be connected to the first and second connecting members such that the magnets connected thereto are distal from the septum. In certain embodiments, the filaments are connected to the first and second connecting members at a central location on the outward-facing surface of the first and second connecting members.

In one embodiment, the first and second magnets are connected to the first and second connecting members via rigid filaments that position the first and second magnets within the nasal passages. In another embodiment, the first and second magnets are connected to the first and second connecting members via flexible filaments that allow the first and second magnets to hang within the nasal passages.

The aforementioned components of the nose filter mounting device may be fabricated from any combination of biocompatible materials known to those of skill in the art. For example, the components may be formed of metal, such as titanium, silver, stainless steel, nitinol, nickel, palladium, or gold, and/or a polymeric material, such as a silicone-based material. Alloys may be used such as cobalt chromium or synthetic materials such as hydroxylapatite. In certain embodiments, the elongated members are formed of one or more materials selected from the group consisting of titanium and gold. In certain embodiments, the first and second magnets are rare-earth magnets.

Filters

In certain embodiments, as shown in FIG. 3, filter elements 114, 116 are provided to mate with the first and second magnets 110, 112 of the nose filter mounting device 100, in the nostrils of a user. Each filter element 114, 116 may include a ferromagnet 132 and a filter 134. As used herein, the term "ferromagnet" refers to materials which form permanent magnets or are attracted to magnets. For example, the ferromagnet may include a rare earth magnet. The design of the filter elements and mounting device advantageously allows a user to position a magnetic filter element in the range of, or near, the first or second magnet, without requiring the user to position or connect the filter manually. The opposing magnetic forces will orient the magnets into an aligned, or straight, configuration automatically.

The filter may be a flexible sheet material. The filter may be formed of one or more filter materials that are known to persons of skill in the art. For example, the filter may be formed of materials that are effective to filter allergens, pollutants, and/or irritants from the air, and allow a patient to breathe through their nostrils. The filter may be sized and shaped such that it creates a barrier within the nostril. For example, the filter may be circular or elliptical in shape. For example, the filter material may include a commercially available filter material that is non-latex, biocompatible, and 100% breathable. The filter may be designed to prevent up to 99% of airborne allergens including pollen, dust, bacteria, pet dander, molds, pollution, and other contaminants.

In one embodiment of the filter elements, the ferromagnet and the filter are separate components. For example, the ferromagnet may be reusable while the filter is made for one-time use, e.g., designed to be changed on a daily basis or as frequently as is required by the quality of inhaled air. For example, the ferromagnet may be operable to secure a separate filter between the ferromagnet and the magnetic disc of a nose filter mounting device. In another embodiment of the filter elements, the ferromagnet 132 is integral with the filter 134. For example, the ferromagnet 132 may be provided in the center of a filter 134, as shown in FIG. 6.

In certain embodiments, as shown in FIG. 3, each filter element 114 has a filter filament 148 extending therefrom. For example, a filter filament may extend from the ferromagnet of a filter element such that when the filter element mates with the first or second magnet of a nose filter device, the filter filament is positioned near the nostril opening. For example, the filament may allow a user to easily remove the filter element by pulling on the filament. The filter filament may be formed of a flexible material, such as a biocompatible silicone-based material. The filter filament may include one or more protuberances that enable gripping by a user. For example, the protuberances may include a knob or tab.

Method

In another aspect, a method for implanting a nose filter mounting device is provided. The nose filter mounting device may be any device as described herein. The method includes providing a pronged article and a second connecting member, piercing the nasal septum of a patient with a septum piercing device, inserting the pronged article through the nasal septum, and positioning the second connecting member on the pronged article.

In one embodiment, as shown in FIG. 1, the pronged article 136 includes two substantially parallel elongated members 102, 104 having first and second ends, a first connecting member 106 joining the two elongated members 102, 104 at the first ends, and a first magnet 110 connected to the first connecting member 106. For example, the elongated members may be joined by the first connected member as described herein. The first connecting member may be substantially perpendicular to the two elongated members. The first magnet may be connected to the first connecting member in any way as described herein.

In one embodiment, the second connecting member 108 has a second magnet 112 connected thereto. For example, the second magnet may be connected to the second connecting member in any way as described herein. For example, the second magnet may be connected to the second connecting member via a filament. In one embodiment, the second connecting member has two apertures therein, the apertures being configured to allow the two elongated members to fit therein. For example, the apertures may have a similar size and shape to the cross-section of the elongated members.

In one embodiment, the step of piercing the nasal septum of a patient includes piercing the nasal septum with a septum piercing device to provide two septum apertures, inserting the pronged article through the two septum apertures, and positioning the second connecting member on the two elongated members such that the two elongated members are joined at the second ends. The nasal septum may be pierced such that the two septum apertures substantially share a horizontal plane. That is, the two apertures may be configured such that the elongated members of the implanted device are substantially perpendicular to the nasal septum and substantially share a horizontal plane. Alternatively, the nasal septum may be pierced such that the two septum apertures substantially share a vertical or other plane.

The step of positioning the second connecting member may include positioning the two apertures of the second connecting member on the two elongated members. In certain embodiments, the method may also include securing the second connecting member on the two elongated members with a mating member positioned at or near the second ends of the two elongated members. The mating member may be any mating member as described herein. For example, the mating member may be integral with the second connecting member. Alternatively, the mating member may include two distinct mating elements, each mating element being operable to secure on the second end of one of the two elongated members.

In one embodiment, the step of piercing a nasal septum includes providing a septum piercing device and inserting the two hollow needles of the septum piercing device through the septum of the patient. As shown in FIG. 5, the septum piercing device 138 may include an elongated portion 140, an end portion 142 sized and shaped to fit inside a patient's nostril, the end portion 142 being located at a first end of the elongated portion 140, and two parallel hollow needles 144, 146 affixed on the end portion 142. The parallel hollow needles may have a cross-section that is sized and shaped similarly to the cross-section of the elongated members. The hollow needles may have a diameter of between about 0.5 mm and about 3 mm. For example, each of the hollow needles may have a diameter of less than about 3 mm, less than about 2 mm, or less than about 1 mm. In one embodiment, the hollow needles may have a diameter of about 1 mm.

In one embodiment, the step of inserting the pronged article includes inserting the two elongated members of the pronged article into the hollow needles of the septum piercing device, and removing the septum piercing device from the nostril, thereby positioning the elongated members of the pronged article within the septum. For example, the pre-measured hollow needles pierce the septum to allow the first connecting member to perfectly align with the apertures of the needles, thereby allowing the parallel elongated members to slide into the hollow needles such that when the piercing device is removed, the elongated members are positioned properly through the septum.

In certain embodiments, the method also includes mating one or more filter elements with the first and/or second magnets. The one or more filter elements may be any filter elements as described herein. For example, the one or more filter elements may each include a ferromagnet and a filter.

This method advantageously may require only topical and local anesthesia for initial device implantation. Additionally, it is believed that this method produces semi-permanent holes in the patient's septum, similar to pierced earring holes, such that the device may be easily removable by the physician. For example, to remove the device, a physician may simply release the mating mechanism, remove the second connecting member from the pronged article, and remove the pronged article from the septum. Similarly, to replace the device, a physician may insert the two elongated members of the pronged article through the two septum apertures and join the second connecting member and mating mechanism at the second ends of the elongated members. The physician may have to use the septum piercing device if the perforations have closed or cannot be easily located in order to replace the device or insert a new one.

Kit

In a third aspect, a kit is provided. In one embodiment, the kit includes a septum piercing device 138, a pronged article 136, and a second connecting member 108. The kit may include any combination of the various piercing devices, pronged articles, and second connecting members described herein.

In one embodiment, the kit also includes a mating member operable to secure the second connecting member at or near the second ends of the two elongated members. The mating member may be any mating member as described herein. In one embodiment, the kit also includes one or more filter elements configured to mate with the first or second magnets. The one or more filter elements may be any filter elements as described herein.

Publications cited herein and the materials for which they are cited are specifically incorporated by reference herein. Modifications and variations of the methods and compositions described herein will be obvious to those skilled in the art from the foregoing detailed description. Such modifications and variations are intended to come within the scope of the appended claims.

I claim:

1. A nose filter mounting device comprising:
   a septum implantation portion configured for implantation across a nasal septum of a user, the septum implantation portion consisting essentially of two substantially parallel elongated members, each elongated member having a first end and a second end and a cross-sectional width less than about 3 mm;
   a first connecting member joining the two elongated members at or near the first ends;
   a second connecting member joining the two elongated members at or near the second ends;
   a first magnet connected to the first connecting member; and
   a second magnet connected to the second connecting member,
   wherein the first and second magnets are configured to mate with filter elements in the nostrils of the user.

2. The device of claim 1, wherein the first connecting member is substantially perpendicular to the two elongated members.

3. The device of claim 1, wherein the second connecting member has two apertures therein, the apertures being configured to fit on the two elongated members.

4. The device of claim 1, further comprising a mating member operable to secure the second connecting member at or near the second ends of the two elongated members.

5. The device of claim 1, wherein the elongated members are substantially cylindrical.

6. The device of claim 1, wherein the first and second magnets are connected to the first and second connecting members via filaments.

7. The device of claim 1, wherein each filter element comprises:
   a ferromagnet; and
   a filter.

8. The device of claim 7, wherein the filter comprises a flexible sheet material that is breathable and capable of filtering pollutants and contaminants.

9. The device of claim 7, wherein the ferromagnet and the filter are separate, the ferromagnet being reusable.

10. The device of claim 7, wherein the ferromagnet is integral with the filter.

11. The device of claim 1, wherein each filter element has a filament extending therefrom, such that when the filter element mates with the first or second magnet, the filament is positioned near the nostril opening.

12. The device of claim 11, wherein the filament comprises one or more protuberances.

13. The device of claim 4, wherein the mating member is integral with the second connecting member.

14. The device of claim 4, wherein the mating member comprises two distinct mating elements, each mating element operable to secure on the second end of one of the two elongated members.

15. The device of claim 1, wherein the first and second magnets comprise rare-earth magnets.

16. The device of claim 1, wherein the elongated members comprise one or more materials selected from the group consisting of titanium, gold, stainless steel, nitinol, palladium, hydroxylapatite, silicon, and cobalt chromium.

17. A kit comprising:
    a septum piercing device comprising:
      an elongated portion;
      an end portion sized and shaped to fit inside the patient's nostril, the end portion located at one end of the elongated portion; and
      two parallel hollow needles affixed on the end portion, the parallel hollow needles each having a diameter of about 3 mm or less;
    a pronged article comprising:
      two substantially parallel elongated members, each elongated member having a first and a second end and a cross-sectional width less than about 3 mm;
      a first connecting member joining the two elongated members at or near the first ends; and
      a first magnet connected to the first connecting member; and
    a second connecting member configured to join the two elongated members at or near the second ends and having a second magnet connected thereto.

18. The kit of claim 17, further comprising a mating member operable to secure the second connecting member at or near the second ends of the two elongated members.

19. The kit of claim 18, wherein the mating member is integral with the second connecting member.

20. The kit of claim 17, wherein the second connecting member has two apertures therein, the apertures being configured to fit on the two elongated members.

21. The kit of claim 17, wherein the first connecting member is substantially perpendicular to the two elongated members.

22. The kit of claim 17, further comprising one or more filter elements configured to mate with the first or second magnets.

23. The kit of claim 22, wherein the one or more filter elements each comprise:
    a ferromagnet; and
    a filter.

24. A nose filter mounting device consisting essentially of:
    two substantially parallel elongated members, each elongated member having a first end and a second end and being configured for implantation across a nasal septum of a user;
    a first connecting member joining the two elongated members at or near the first ends;
    a second connecting member joining the two elongated members at or near the second ends;
    a first magnet connected to the first connecting member; and
    a second magnet connected to the second connecting member,
    wherein the first and second magnets are configured to mate with filter elements in the nostrils of the user.

25. The device of claim 24, wherein the first connecting member is substantially perpendicular to the two elongated members.

26. The device of claim 24, wherein the second connecting member has two apertures therein, the apertures being configured to fit on the two elongated members.

27. The device of claim 24, further comprising a mating member operable to secure the second connecting member at or near the second ends of the two elongated members.

28. The device of claim 27, wherein the mating member is integral with the second connecting member.

29. The device of claim 27, wherein the mating member comprises two distinct mating elements, each mating element operable to secure on the second end of one of the two elongated members.

* * * * *